(12) United States Patent
Cohen et al.

(10) Patent No.: US 9,008,756 B2
(45) Date of Patent: Apr. 14, 2015

(54) MAPPING SYSTEM AND METHOD FOR MAPPING A TARGET CONTAINING TISSUE

(75) Inventors: Gil Cohen, Jerusalem (IL); Dan Hashimshony, Givat Ada (IL)

(73) Assignee: Dune Medical Devices Ltd., Caesarea (IL)

( * ) Notice: Subject to any disclaimer, the term of this patent is extended or adjusted under 35 U.S.C. 154(b) by 164 days.

(21) Appl. No.: 12/964,511

(22) Filed: Dec. 9, 2010

(65) Prior Publication Data

US 2011/0313284 A1 Dec. 22, 2011

Related U.S. Application Data

(63) Continuation of application No. PCT/IL2009/000577, filed on Jun. 10, 2009.

(60) Provisional application No. 61/060,526, filed on Jun. 11, 2008.

(51) Int. Cl.
*A61B 5/00* (2006.01)
*A61B 19/00* (2006.01)

(52) U.S. Cl.
CPC ..... *A61B 19/5244* (2013.01); *A61B 2019/5268* (2013.01); *A61B 2019/5272* (2013.01); *A61B 2019/5287* (2013.01); *A61B 2019/5408* (2013.01)

(58) Field of Classification Search
USPC .......... 600/407, 424, 426, 427, 429; 606/130
See application file for complete search history.

(56) References Cited

U.S. PATENT DOCUMENTS

| | | | |
|---|---|---|---|
| 4,849,692 A | 7/1989 | Blood | |
| 4,945,305 A | 7/1990 | Blood | |
| 5,615,132 A | 3/1997 | Horton et al. | |
| 6,109,270 A | 8/2000 | Mah et al. | |
| 6,501,981 B1 * | 12/2002 | Schweikard et al. | 600/427 |
| 6,813,515 B2 | 11/2004 | Hashimshony | |
| 6,833,814 B2 | 12/2004 | Gilboa et al. | |
| 7,082,325 B2 | 7/2006 | Hashimshony et al. | |
| 7,184,824 B2 | 2/2007 | Hashimshony | |
| 2001/0027272 A1 | 10/2001 | Saito et al. | |
| 2002/0044631 A1 | 4/2002 | Graumann et al. | |
| 2002/0104376 A1 | 8/2002 | Danyluk et al. | |
| 2002/0180306 A1 | 12/2002 | Hunt et al. | |
| 2003/0138378 A1 | 7/2003 | Hashimshony | |
| 2003/0187366 A1 | 10/2003 | Hashimshony | |

(Continued)

FOREIGN PATENT DOCUMENTS

WO 2008035271 A2 3/2008
WO 2008072238 A2 6/2008

OTHER PUBLICATIONS

International Search Report, mailed Jan. 19, 2010, from PCT/IL2009/000577, filed on Jun. 10, 2009.

*Primary Examiner* — Ruth S Smith
(74) *Attorney, Agent, or Firm* — Browdy and Neimark, PLLC

(57) ABSTRACT

A mapping system (200) including: (a) at least one external marker (210,212,214,216) adapted for positioning outside a target (520) to define a target context; (b) at least one target marker (230) adapted for positioning with the target; (c) a data acquisition tool (221) configured to provide position coordinates for at least one data point (220) at the target (520); and (d) a registration module (300) adapted to output position coordinates of said at least one data point relative to at least a portion of the target context.

12 Claims, 8 Drawing Sheets

(56) References Cited

U.S. PATENT DOCUMENTS

| | | |
|---|---|---|
| 2004/0243148 A1 | 12/2004 | Wasielewski |
| 2005/0021019 A1 | 1/2005 | Hashimshony et al. |
| 2006/0253107 A1 | 11/2006 | Hashimshony et al. |
| 2006/0264738 A1 | 11/2006 | Hashimshony et al. |
| 2007/0032739 A1 | 2/2007 | Hashimshony et al. |
| 2007/0032747 A1 | 2/2007 | Hashimshony et al. |
| 2007/0179397 A1 | 8/2007 | Hashimshony et al. |
| 2007/0255169 A1 | 11/2007 | Hashimshony et al. |
| 2007/0260156 A1 | 11/2007 | Hashimshony |
| 2007/0280423 A1 | 12/2007 | Schmidt |

* cited by examiner

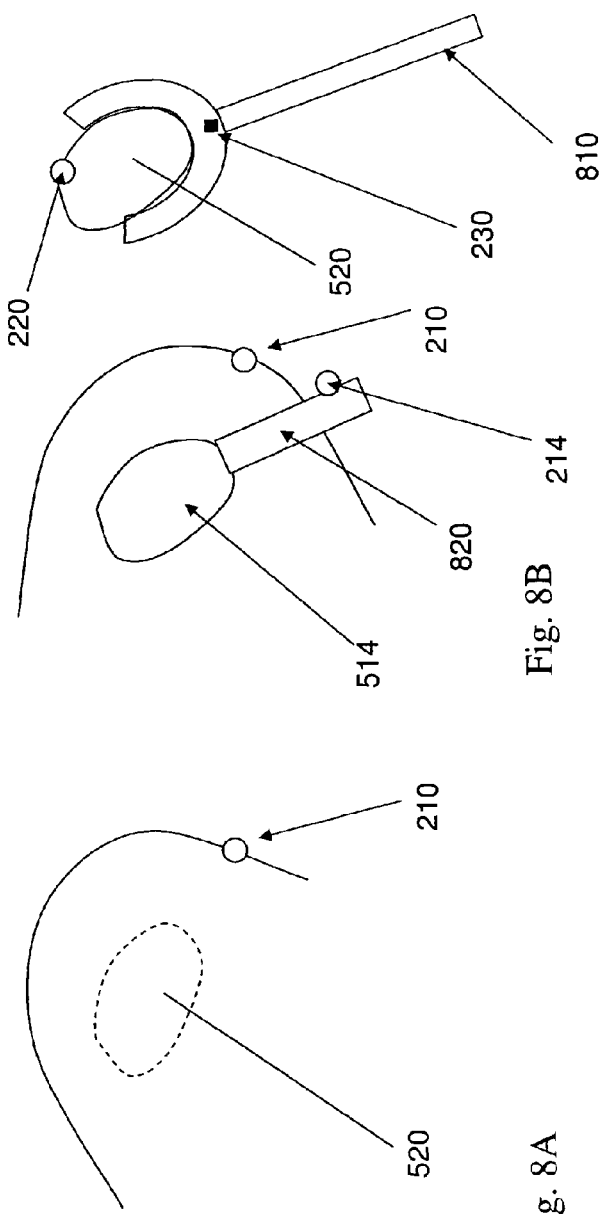
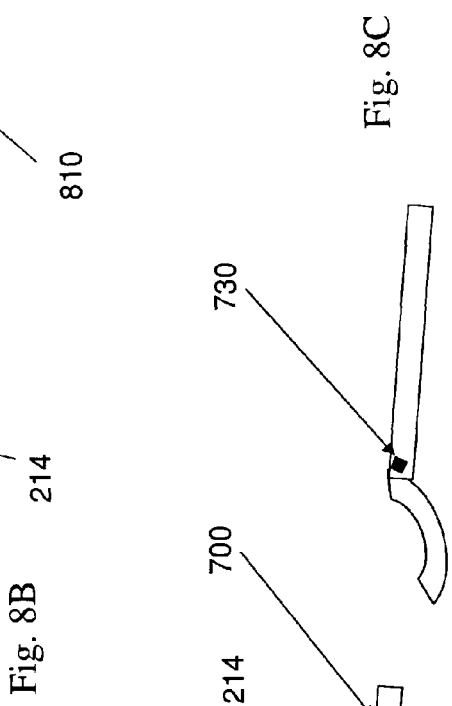
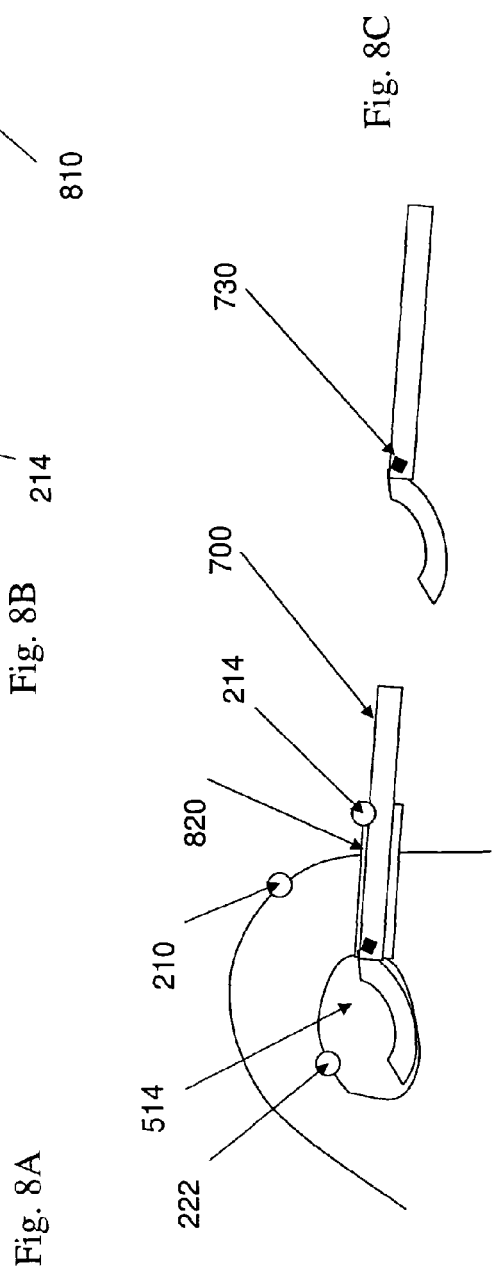

MAPPING SYSTEM AND METHOD FOR MAPPING A TARGET CONTAINING TISSUE

RELATED APPLICATIONS

This application is a Continuation of PCT application serial number PCT/IL2009/000577 filed on Jun. 10, 2009 which claims priority to U.S. provisional application Ser. No. 61/060,526 filed on Jun. 11, 2008 both of which are incorporated herein by reference in their entirety.

FIELD OF THE INVENTION

This invention relates to provision of intrabody coordinates, for example in conjunction with a medical procedure.

BACKGROUND OF THE INVENTION

In some surgical procedures (e.g. tumor resection) a mass of biological material is removed as part of a therapy plan. The removed mass is analyzed to determine whether margins are clean (i.e. free of abnormal cells). In cases where margins are not clean, removal of additional tissue is indicated.

U.S. Pat. No. 6,109,270 describes a measurement concept with a multi-modality instrument for tissue identification in real-time neuro-surgical applications. U.S. Pat. Nos. 6,813,515; 7,082,325 and 7,184,824 U.S. Patent Applications published as 20070260156; 20070255169; 20070179397; 20070032747; 20070032739; 20060264738; 20060253107; 20050021019; 20030187366 and 20030138378 describe tools systems and methods useful in assessing tissue type and/or identifying tumor margins. U.S. Pat. No. 5,615,132 describes a method and apparatus for determining position and orientation of a moveable object using accelerometers.

U.S. Pat. No. 6,833,814 describes an intrabody navigation system for medical applications in which three planar antennas that at least partly overlap are used to transmit electromagnetic radiation simultaneously. PCT application IL 2007/001539 describes apparatus for analysis of a substrate.

US 2004/0243148 by Wasielewski, which is fully incorporated herein by reference, includes a review of source and sourceless sensors including examples of commercially available products in paragraphs 0087-0103 as well as reference to earlier US patent applications 2002/0180306 and 2002/0104376 which are each fully incorporated herein by reference.

Ascension Technology Corp. (Burlington Vt., USA) markets a guide for localizing medical instruments with 3D magnetic tracking as "3D Guidance™ Medsafe".

Traxtal Inc. (Toronto, Ontario, Canada) markets probes suitable for registration and general navigation purposes and skin mounted patches suitable for tracking a point on a patient.

Northern Digital hie. (NDI; Waterloo, Ontario Canada) markets electromagnetic tracking components (Aurora®) and optical tracking components (Optitrak® and/or Polaris®). Crossbow Technology hie. (San Jose, Calif., USA) markets a wide range of sensors which rely on accelerometry, angular rate measurement (gyros), magnetometry and GPS.

SUMMARY OF THE INVENTION

An aspect of some embodiments of the invention relates to receiving an input in the form of a first set of position coordinates defined relative to a target marker provided with a tissue mass and providing an output in the form of a second set of position coordinates defined relative to at least one external marker provided outside the tissue mass. In some exemplary embodiments of the invention, at least three markers external are provided. In some exemplary embodiments of the invention, the externally markers are provided in and/or on a body of a subject from whom the tissue mass is removed. In other exemplary embodiments of the invention, the external markers are deployed in proximity to the subject, but not in contact with the subject's body.

Optionally, the target marker is positioned within the target (e.g. approximately at a geometric center, on a surface of the target, at a location within the target suspected of being malignant) or on a device used to remove the target). According to exemplary embodiments of the invention, the target marker maintains a fixed spatial relationship with respect to the target.

Optionally, the second set of position coordinates is defined relative to less than all of the external markers. In some exemplary embodiments of the invention, the second set of position coordinates is defined relative to a closest of the external markers. Optionally, the tissue mass is in situ, partially excised or fully excised. An aspect of some embodiments of the invention relates to analytic circuitry adapted to determine which external marker(s) should be employed in providing the output. In various exemplary embodiments of the invention, external markers which have moved from their original position or have remained in their original position are selected. An aspect of some embodiments of the invention relates to identifying pathology on a portion of a target tissue mass and removing additional tissue from a corresponding portion of a body cavity from which the target tissue mass was removed. Optionally, the target tissue mass is a biopsy sample or surgically excised tissue mass. In various exemplary embodiments of the invention, the sample can be taken from breast, prostate, lung, liver, esophagus, trachea or intestine.

In some exemplary embodiments of the invention, there is provided a mapping system, the system includes:

(a) at least one external marker adapted for positioning outside a target to define a target context; (b) at least one target marker adapted for positioning with the target;

(c) a data acquisition tool configured to provide position coordinates for at least one data point at the target; and (d) a registration module adapted to output position coordinates of the at least one data point relative to at least a portion of the target context. Optionally, the at least one data point at the target is on a surface of the target.

Optionally, the position coordinates of the at least one data point provided by the data acquisition tool are defined relative to the at least one target marker.

Optionally, the at least one external marker includes at least three external markers. Optionally, the registration module includes analytic circuitry adapted to: receive a first data input includes a position of the at least one target marker relative to the external marker and a second data input includes a relative position of the data acquisition tool with respect to the at least one target marker; and process the two data inputs to produce the output.

Optionally, the registration module is provided as software configured for installation on an object selected from a computer, a personal digital assistant and a remote server. Optionally, the position coordinates include vectorial position information includes a distance, an angle of elevation and an angle of rotation.

Optionally, the position coordinates include Cartesian coordinates.

Optionally, the at least a portion of the target context includes at least one of the at least one external markers. Optionally, the system includes a reporting module.

Optionally, the system includes a guidance module adapted to: receive the output of the registration module and position coordinates of an operative device; and issue guidance instructions to guide the operative device to a location of the target context corresponding to the data point at the target.

Optionally, the guidance instructions include at least one of an audio signal and a visual signal.

Optionally, the guidance instructions include operating instructions for a robotic device.

In some exemplary embodiments of the invention, there is provided a method of mapping a point on a target to a corresponding point in a context of the target, the method includes:

(a) defining a target context by positioning at least one contextual marker external to the target and at least one target marker with the target;

(b) determining a location of the at least one target marker relative to contextual marker;

(c) altering a spatial relationship between the target and the contextual marker; (d) recording position coordinates for at least one data point at the target; and (e) transforming the position coordinates of the at least one data point to translated coordinates defined relative the contextual marker.

Optionally, the at least one data point at the target resides on a surface of the target.

Optionally, the at least one contextual marker includes at least three contextual markers. Optionally, the location of the at least one target marker relative to the at least one contextual markers is expressed as a distance, an angle of elevation and an angle of rotation.

Optionally, the location of the at least one target marker relative to the at least one contextual markers is expressed as Cartesian coordinates. Optionally, the method includes outputting the transformed co-ordinates.

Optionally, the method includes using the output of the transformed coordinates to guide an operative device to a location in the target context corresponding to the data point at the target.

In some exemplary embodiments of the invention, there is provided a mapping registration apparatus, the apparatus includes:

(a) a context determination module configured to determine a location of at least one target marker at a target relative to at least one contextual marker outside the target and output a series of relative locations to a memory;

(b) a data receiver configured to receive position coordinates relative to the at least one target marker for at least one data point at the target and relay the relative position coordinates to the memory; and (c) analytic circuitry adapted to receive data stored in memory and transform the relative position coordinates of the at least one data point to translated coordinates defined relative to at least one of the at least one contextual markers. Optionally, the relative locations are defined in terms of distance, angle of elevation and angle of rotation.

Optionally, the position coordinates relative to the at least one target marker for at least one data point at the target are defined in terms of distance, angle of elevation and angle of rotation. Optionally, the apparatus includes a clinical data input module adapted to receive clinical data for at least some of the position coordinates relative to the at least one target marker for at least one data point at the target and link the clinical data to the relative position coordinates in the memory.

In some exemplary embodiments of the invention, there is provided a contextual position indicator, the indicator includes:

(a) a position indication module adapted to provide a position output signal;

(b) a signal port adapted to relay the output signal to an external device; and (c) an adhesive surface adapted to adhere to a subject.

Optionally, the position output signal defines a relative position of at least one other position indicator relative to the contextual position indicator. Optionally, the indicator includes a removable cover on the adhesive surface.

Optionally, the signal port relays the output signal to the external device via a physical connection.

Optionally, the signal port relays the output signal to the external device via a wireless connection.

In some exemplary embodiments of the invention, there is provided a mapping system, the system includes: (a) a context definition tool configured to provide position coordinates for at least one data point outside a target to define a target context;

(b) at least one target marker adapted for positioning with the target;

(d) a registration module adapted to output position coordinates of at least one point defined by the context definition tool relative to the at least one target marker. In some exemplary embodiments of the invention, there is provided a method of mapping a point on a target to a corresponding point in a context of the target. The method includes: (a) defining a target context by positioning at least one contextual marker external to the target and at least one target marker at the target; (b) determining a relative location of the at least one target marker with respect to the contextual marker and storing the relative location in a computer memory; (c) altering a spatial relationship between the target and the contextual marker; (d) recording position coordinates for at least one data point at the target in the computer memory; and (e) transforming the position coordinates of the at least one data point to translated coordinates defined relative to the contextual marker using a data processor. Optionally, the method includes outputting the transformed co-ordinates to a user interface.

Optionally, the method includes using the output of the transformed coordinates to guide an operative device to a location in the target context corresponding to the data point at the target.

Optionally, the user interface graphically depicts the data point at the target relative to the contextual marker.

Unless otherwise defined, all technical and scientific terms used herein have the same meaning as commonly understood by one of ordinary skill in the art to which this invention belongs. Although suitable methods and materials are described below, methods and materials similar or equivalent to those described herein can be used in the practice of the present invention. In case of conflict, the patent specification, including definitions, will control. All materials, methods, and examples are illustrative only and are not intended to be limiting.

For purposes of this specification and the accompanying claims, the phrase "external marker" or "contextual marker" refers to a marker located outside a target. For purposes of this specification and the accompanying claims, the phrase "target marker" refers to a marker located on or within a target or at a fixed spatial relationship with respect to the target. Optionally, a target marker is placed at or near a center of mass of the target.

For purposes of this specification and the accompanying claims, the term "target" refers to an object that is to be moved relative to at least part of its context. The term target includes, but is not limited to a biopsy sample, a surgically excised tissue mass and a block of stone removed from a quarry.

For purposes of this specification and the accompanying claims, the term "context" refers to a group of points which are not part of the target and can be used to define target position and orientation.

For purposes of this specification and the accompanying claims, the term "marker" should be construed in its broadest possible sense so that it includes both passive markers and active markers. Markers according to various exemplary embodiments of the invention are optionally oriented markers defined with five degrees of freedom (e.g. three position co-ordinates, an angle of elevation and an angle of rotation).

For purposes of this specification and the accompanying claims "passive markers" are markers which do not broadcast a signal. One exemplary passive marker is an X-ray opaque object (e.g. steel bead). Positions of X-ray opaque objects can be localized, for example, using computer assisted tomography. Another exemplary passive marker is an ultrasound reflector. Positions of ultrasound reflectors can be localized, for example, using ultrasound transducers. For purposes of this specification and the accompanying claims "active markers" are markers which transmit or broadcast a signal. Exemplary active markers include, but are not limited to radio frequency, infrared, magnetic field, and microwave transmitters. Positions of active markers can be localized using one or more appropriate receivers configured to measure both direction and amplitude of incident signals. In some exemplary embodiments of the invention, active magnetic field markers are employed. In some exemplary embodiments of the invention, active and/or passive optical markers are employed. In some exemplary embodiments of the invention, active accelerometry markers are employed. In some exemplary embodiments of the invention, active angular rate measurement (gyros), magnetometry and/or GPS markers are employed.

As used herein, the terms "comprising" and "including" or grammatical variants thereof are to be taken as specifying inclusion of the stated features, integers, actions or components without precluding the addition of one or more additional features, integers, actions, components or groups thereof. This term is broader than, and includes the terms "consisting of and "consisting essentially of as defined by the Manual of Patent Examination Procedure of the United States Patent and Trademark Office.

The phrase "consisting essentially of or grammatical variants thereof when used herein are to be taken as specifying the stated features, integers, steps or components but do not preclude the addition of one or more additional features, integers, steps, components or groups thereof but only if the additional features, integers, steps, components or groups thereof do not materially alter the basic and novel characteristics of the claimed composition, device or method.

The term "method" refers to manners, means, techniques and procedures for accomplishing a given task including, but not limited to, those manners, means, techniques and procedures either known to, or readily developed from known manners, means, techniques and procedures by practitioners of architecture and/or computer science.

Implementation of the method and system of the present invention involves performing or completing selected tasks or steps manually, automatically, or a combination thereof. Moreover, according to actual instrumentation and equipment of preferred embodiments of methods, apparatus and systems of the present invention, several selected steps could be implemented by hardware or by software on any operating system of any firmware or a combination thereof. For example, as hardware, selected steps of the invention could be implemented as a chip or a circuit. As software, selected steps of the invention could be implemented as a plurality of software instructions being executed by a computer using any suitable operating system. In any case, selected steps of the method and system of the invention could be described as being performed by a data processor, such as a computing platform for executing a plurality of instructions.

According to various exemplary embodiments of the invention, adaptation of various modules described hereinbelow can be implemented at the level of hardware, firmware or software.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings:

In order to understand the invention and to see how it may be carried out in practice, embodiments will now be described, by way of non-limiting example only, with reference to the accompanying figures. In the figures, identical and similar structures, elements or parts thereof that appear in more than one figure are generally labeled with the same or similar references in the figures in which they appear.

Figure 1:
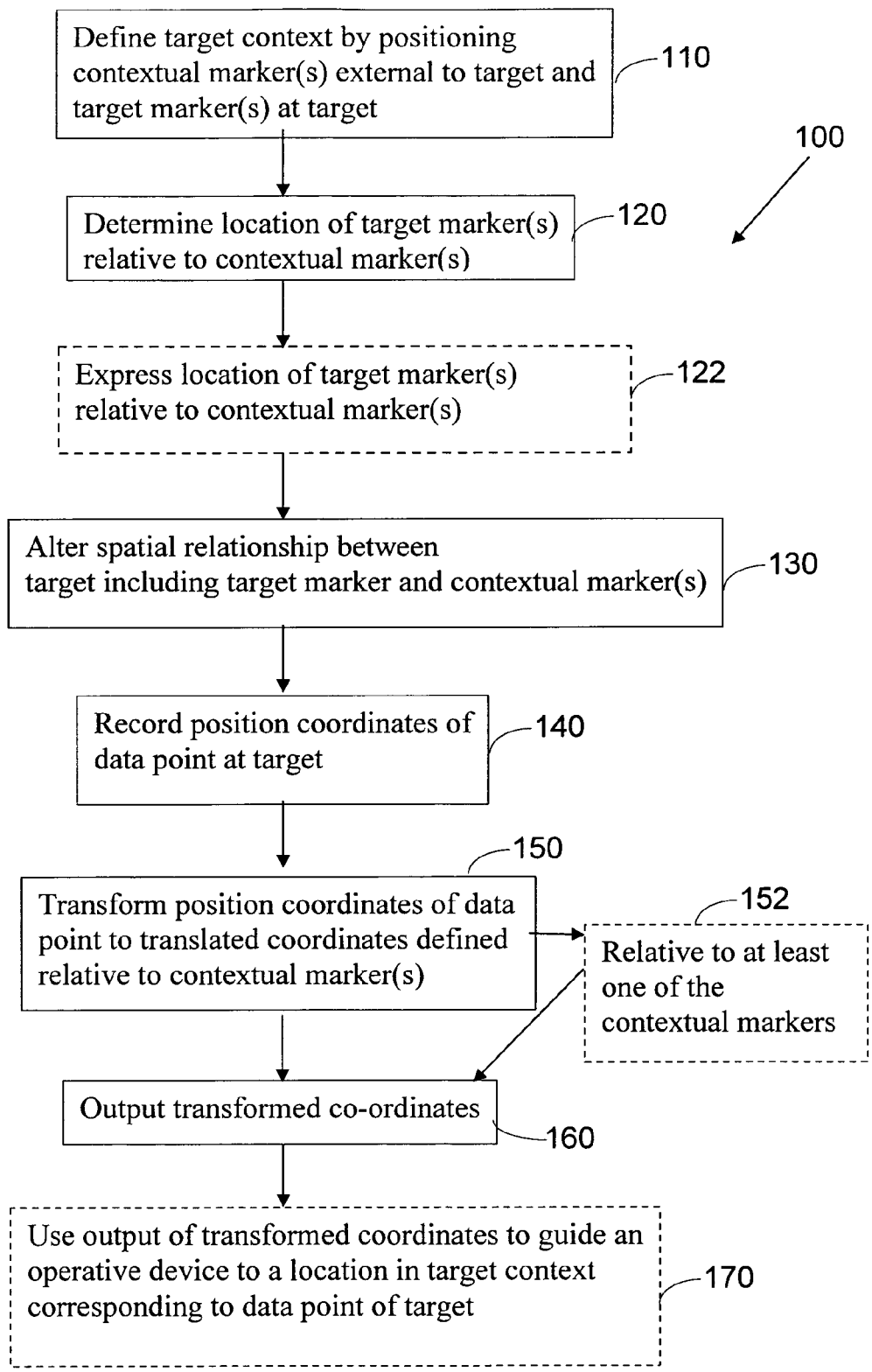
Figure 2:
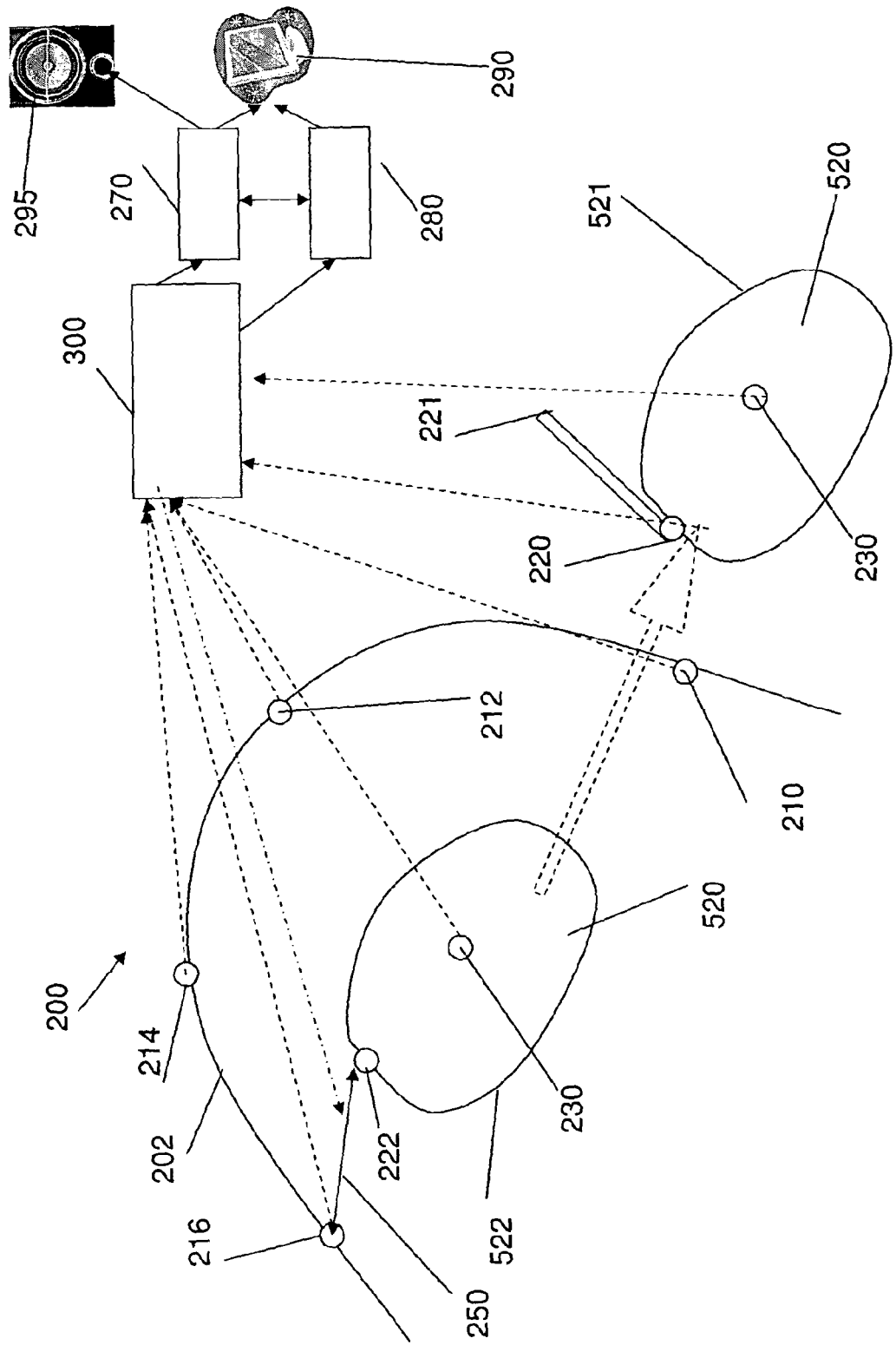
Figure 3:
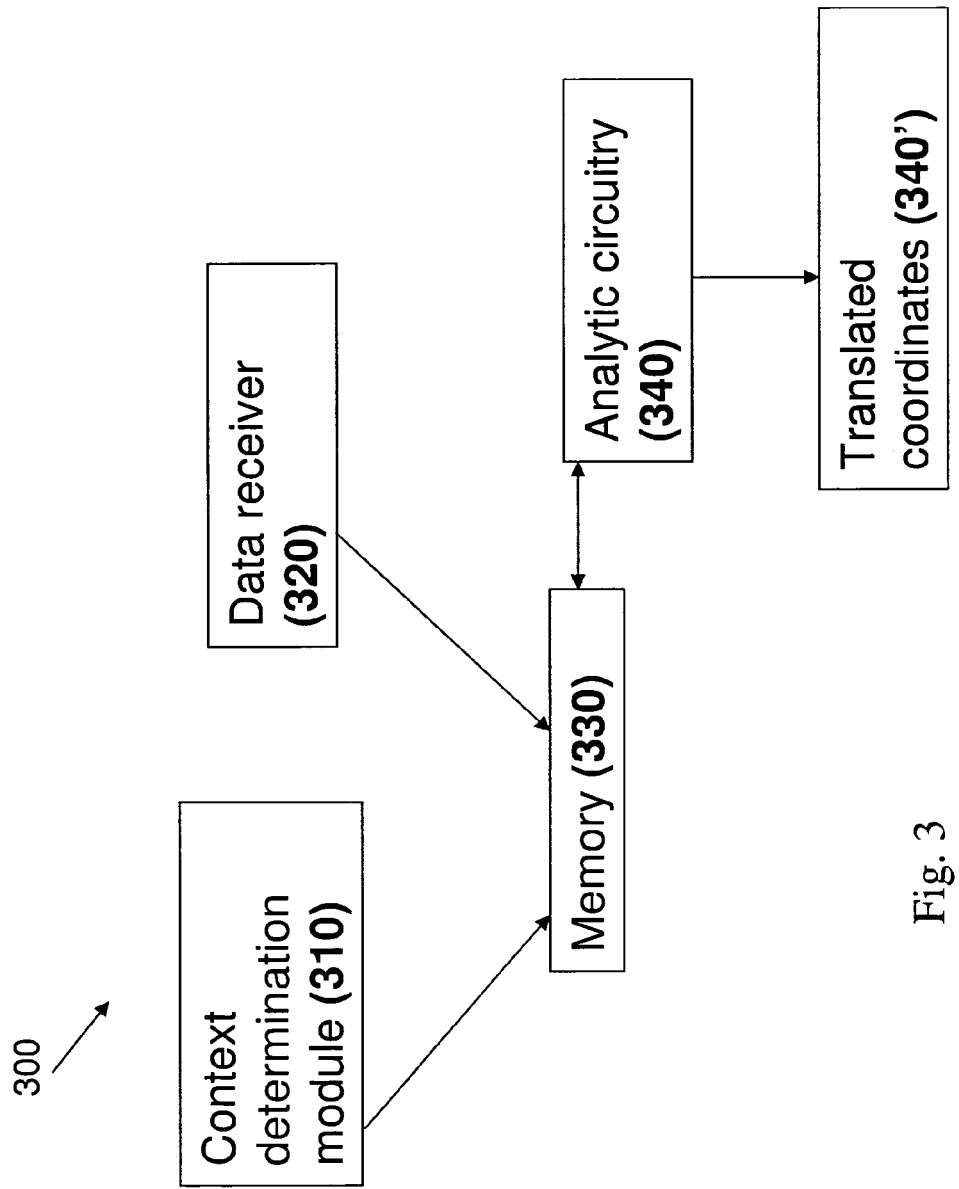
Figure 4:
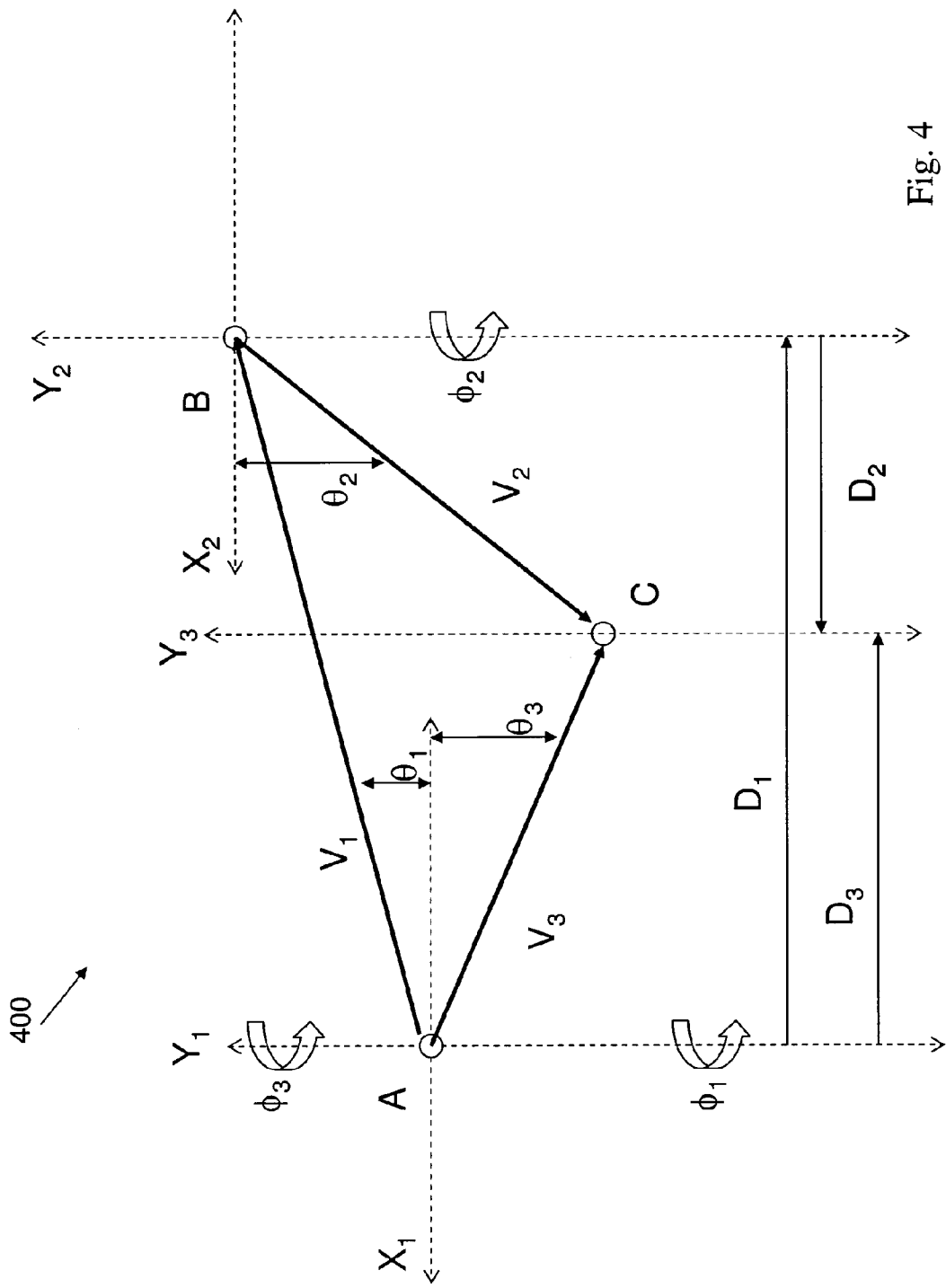
Figures 5A, 5B:
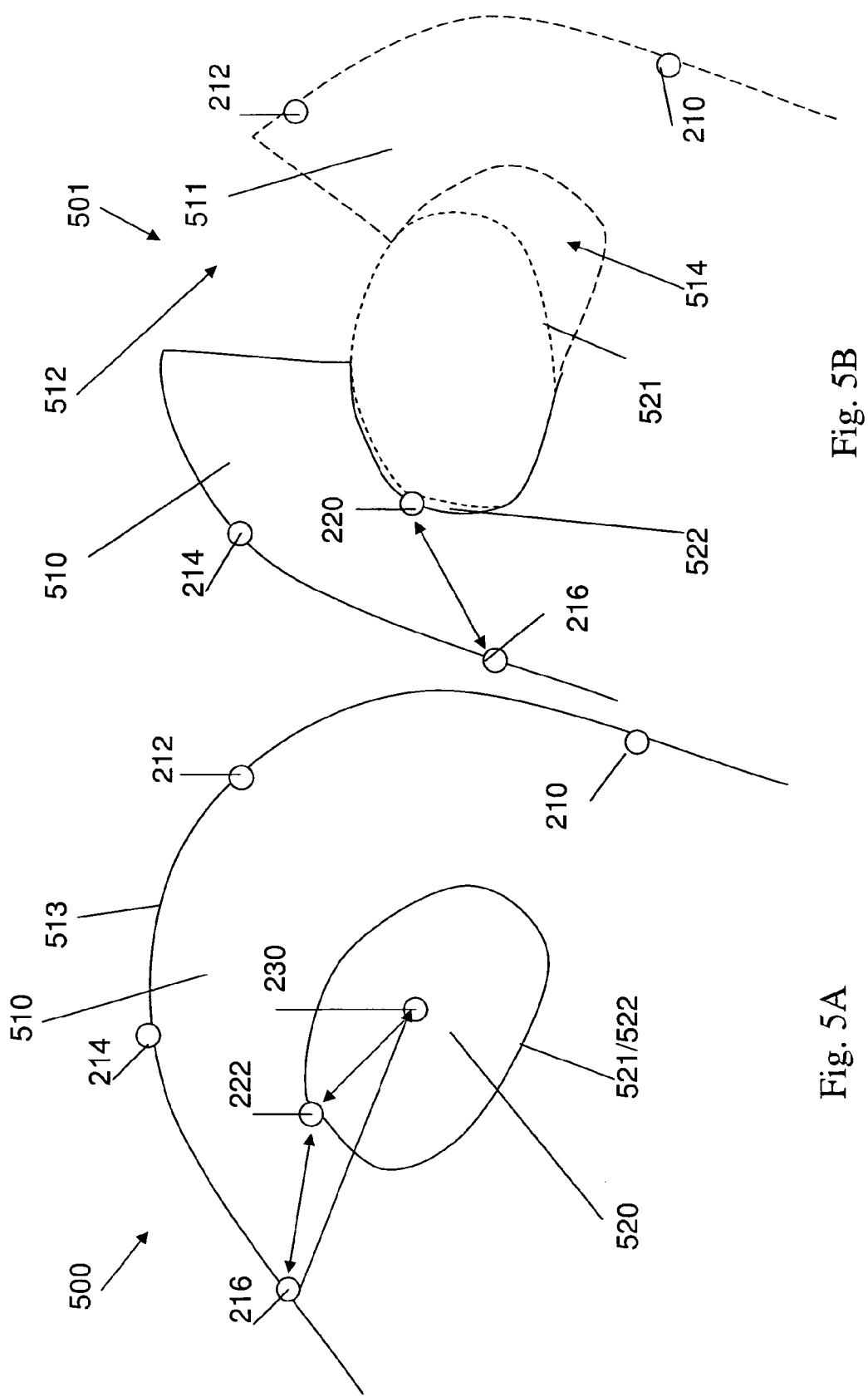
Figure 6:
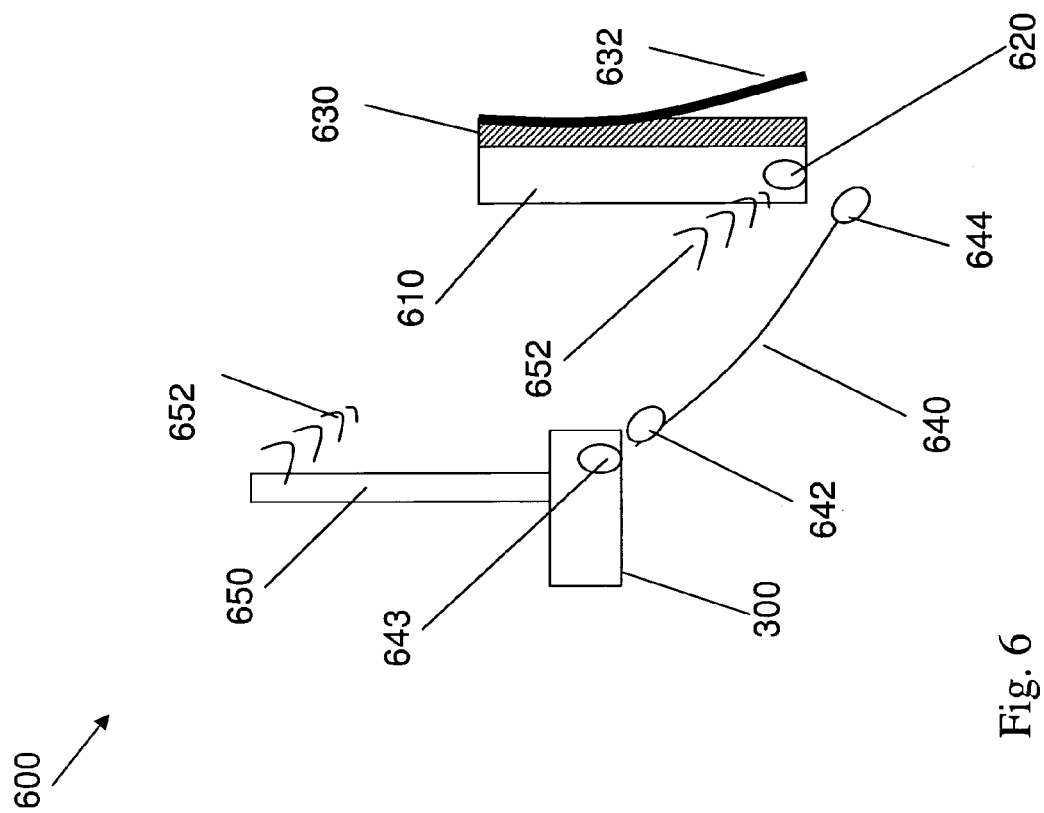
Figure 7:
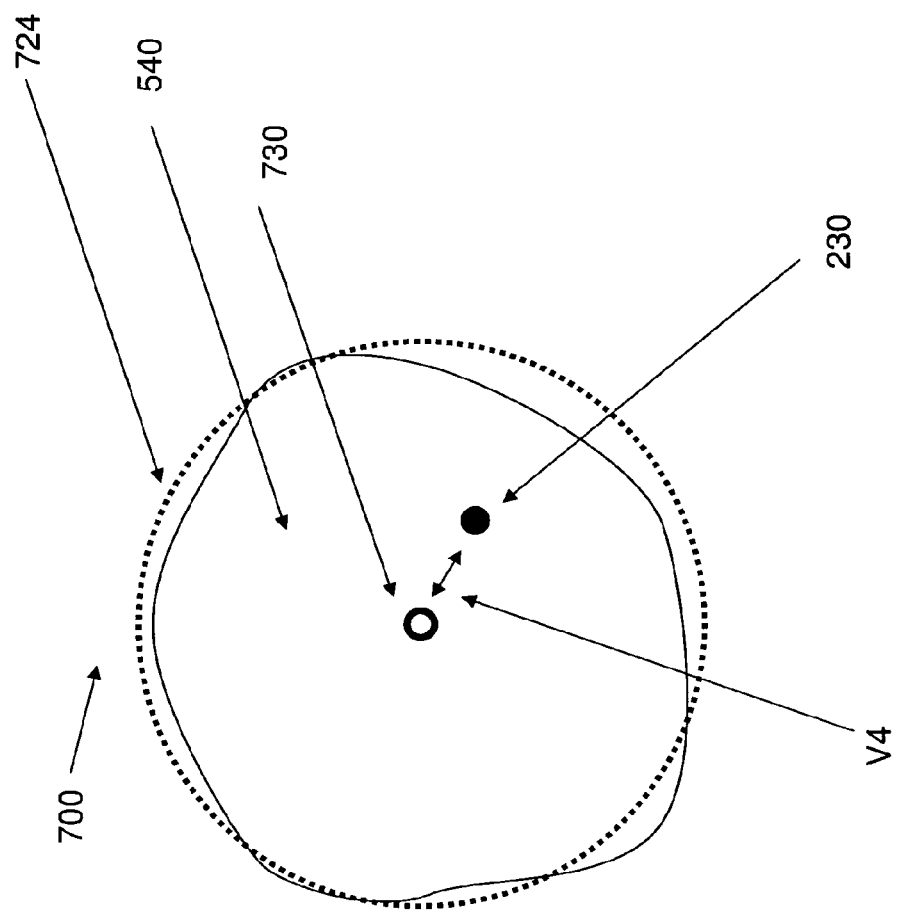

Dimensions of components and features shown in the figures are chosen primarily for convenience and clarity of presentation and are not necessarily to scale. The attached figures are:

FIG. 1 is simplified flow diagram of a method according to some embodiments of the invention;

FIG. 2 is a schematic representation of a system according to some embodiments of the invention;

FIG. 3 is a schematic representation of a mapping registration apparatus suitable for use in some embodiments of the system of FIG. 2;

FIG. 4 is a schematic representation of addition of vectors with two different origins;

FIGS. 5A and 5B are schematic representations illustrating exemplary spatial relationships of position indicators before and after excision of a tissue sample respectively;

FIG. 6 is a schematic representation of an exemplary contextual position indicator according to some embodiments of the invention;

FIG. 7 is a schematic representation of an apparatus according to some embodiments of the invention; and FIGS. 8A, 8B and 8C are schematic representation of apparatus according to additional embodiments of the invention.

DETAILED DESCRIPTION OF THE PREFERRED EMBODIMENTS

Embodiments of the invention relate to apparatus, systems and methods for correlating between a location on a target tissue mass and a matching location on/in a body of a subject but not on the target tissue mass. Optionally, the invention is useful in cases where the spatial relationship between at least a portion of the target tissue mass and surrounding contextual tissue is altered.

Specifically, some embodiments of the invention can be used to indicate what portion of an inner wall of a cavity formed by removal or exposure of the target tissue mass (e.g. a surgically excised mass or biopsy sample) corresponds to a pathological (non-clear, or non-clean) margin on the target tissue mass. The principles and operation of a systems and/or apparatus and/or methods according to exemplary embodiments of the invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Exemplary Mapping Method

FIG. 1 is simplified flow diagram of an exemplary method 100 of mapping a point on a target to a corresponding point in a context of the target according to some exemplary embodiments of the invention. Depicted method 100 includes defining 110 a target context. In some exemplary embodiments of the invention, definition 100 is achieved by positioning at least one contextual marker external to the target and a target marker with the target. Optionally, at least three contextual markers are employed. In some exemplary embodiments of the invention, three or more contextual markers are deployed surrounding at least a portion of the target believed to be of interest. Optionally, four, five, six or seven or more contextual markers are deployed at similar angular displacements with respect to a portion of the target believed to be of interest. In those exemplary embodiments of the invention which employ four or more contextual markers, at least one of the contextual markers is positioned in a different plane from the first three markers. Optionally, deployment of contextual markers in different planes contributes to an increase in accuracy of correlation between the location on the target tissue mass and the matching location on/in a body of the subject. In some exemplary embodiments of the invention, contextual markers are deployed in a three dimensional array which surrounds as great a portion of the target tissue mass as can be practically achieved. Optionally, the three dimensional array include contextual markers located on an external surface of the subject (e.g. on the back, clavicle or sternum) and/or internal surfaces (e.g. lumen) of the subject and/or implanted contextual markers in proximity to the target.

According to depicted exemplary method 100 a location of one or more target markers relative to the contextual marker is determined 120. In some exemplary embodiments of the invention, determination 120 is relative to one or more of the contextual markers. Optionally, the location is stored in a computer memory. In some exemplary embodiments of the invention, the stored location is defined in relative terms. In those exemplary embodiments of the invention, where more than one target marker is employed, a geometric center of the markers can serve as a basis for calculation. Alternatively or additionally, in those exemplary embodiments of the invention, where more than one target marker is employed, each of the markers selectively can be used as a separate basis for calculation of relative position coordinates. In cases where multiple contextual markers are employed, a separate determination 120 of relative location of the target marker is made for each contextual marker. Methodology for determination 120 of relative location can rely on any position determination technology known in the art. Determination 120 serves to establish a context of the target tissue mass in which the target marker is placed relative to the contextual markers. Optionally, location of the target marker relative to the contextual marker is expressed 122, for example as a distance, an angle of elevation and an angle of rotation and/or as differences in Cartesian coordinates, or other coordinate systems.

Once determination 120 is complete, a spatial relationship between the target and the contextual marker can be altered 130. In some exemplary embodiments of the invention, alteration 130 exposes at least a portion of a surface of the target. Optionally, the target is completely excised and its entire surface is exposed.

Depicted exemplary method 100 includes recording 140 position coordinates for at least one data point on a surface of the target. In some exemplary embodiments of the invention, recording 140 of the data points is performed in a memory of a data processing device such as a computer. Optionally, storage is in the same memory as the relative locations determined at 120. In some exemplary embodiments of the invention, the position coordinates are correlated to additional data pertaining to the data point (e.g. pathology status). Alternatively or additionally, the position coordinates of the data point relative to the target marker is expressed as a location defined by a distance, an angle of elevation and an angle of rotation.

In some exemplary embodiments of the invention, the position coordinates determined at 140 are transformed 150 to translated coordinates defined relative to the contextual marker. Typically, the transforming is performed by a data processor. Optionally, this transformation employs a vectorial addition algorithm. In some exemplary embodiments of the invention, the transformed coordinates are provided relative to at least one of at least three contextual markers 152. Optionally, a decision is made about which contextual markers to include and/or exclude when performing transformation 150.

In some exemplary embodiments of the invention, the translated coordinates are output 160. Output can be, for example, numeric (e.g. to a display or a memory storage), and/or graphic (e.g. as a vector or point on a display) and/or audible (e.g. pitch and/or pulse rate for angle, amplitude for distance). Alternatively or additionally, translated coordinates can be output as printed data and/or written to machine readable media (e.g. CD-ROM or DVD).

In some exemplary embodiments of the invention, output 160 is to a user interface. Optionally, the user interface graphically depicts the data point(s) at the target relative to the contextual marker.

In some exemplary embodiments of the invention, output 160 of transformed coordinates is used 170 to guide an operative device to a location in said target context corresponding to said data point on said surface of said target.

Operative devices according to various exemplary embodiments of the invention include tools which make physical contact with a tissue in the target context (e.g. physical ablation tools, excision tools and biopsy tools) and energy sources which focus energy on a tissue in the target context without necessarily physically contacting the tissue (e.g. an external beam radiation source, ultrasound cavitation device). According to various exemplary embodiments of the invention energy sources can be further divided into those which are relatively close proximity to the target, such as brachytherapy seeds, RF ablation tools or ultrasound cavitation devices, and those which operate at a great distance from the target such as external beam radiation sources. According to various exemplary embodiments of the invention guidance of an operative device indicates aiming energy produced by the operative device at a specified location and/or moving the device itself relative to the target context.

In this way, method 100 can aid an operator in returning to a specific point and/or a location at the "tissue context", for example on an inner wall of a cavity and/or an exposed tissue surface formed by excision of tissue. This specific point and/or a location may correspond to a point and/or a location for which the corresponding point and/or a location on the excised tissue mass were analyzed, for example by a pathological analysis, and were identified as requiring removal of additional tissue at their location. Similar strategies can be employed in non-medical contexts such as rock quarrying and mining.

Contextual markers can be kept/can remain in place/intact for hours, days, weeks or even months. The persistent nature of the contextual markers means that 170 can be performed at various times, following the time when 130 has occurred. In some exemplary embodiments of the invention, 170 occurs in the operating room, during the same operation. In other exemplary embodiments of the invention, 170 occurs when an additional surgical procedure is performed, following the availability of additional information regarding the target. In non-medical applications, the contextual markers can be left in place until additional data is received, for example from a geologic and/or agronomic analysis.

Exemplary Mapping System

FIG. 2 is a schematic representation of an exemplary mapping system 200 according to some embodiments of the invention. Depicted exemplary mapping system 200 includes at least one external marker, optionally two or three or more external markers (Four are pictured: 210, 212, 214 and 216) adapted for positioning outside a target to define a target context. Adaptation for positioning can vary according to tissue type where the marker is to be positioned and may include, for example, provision of a specific shape, protuberances, surface roughness, adhesive or bio-adhesive on the marker. In the depicted embodiment external markers 210, 212, 214 and 216 are positioned on a skin surface 202 of tissue surrounding a target 520 to be excised. Optionally, markers 210, 212, 214 and 216 are not co-planar. It is noted that one or more of external markers 210, 212, 214 and 216 can be deployed below skin surface 202 so long as they are outside target 520. Optionally, target 520 is removed during a biopsy procedure.

System 200 also includes a target marker 230, or markers, adapted for positioning in target 520. Adaptation can be, for example as described hereinabove. Relative positions of target marker 230 and external markers 210, 212, 214 and 216 can be determined using relevant portions of method 100 as described above to determine a target context.

Following alteration 130 (represented by dotted hollow arrow) of a spatial relationship between target marker 230 and external markers 210, 212, 214 and 216 a data acquisition tool 221 configured to provide position coordinates for at least one data point 220 at target 520 (e.g. on a surface 521 thereof) is operated. Surface 521 of target 520 corresponds to an inner surface 522 of a cavity created by removal of target 520.

Depicted exemplary system 200 includes a registration module 300 adapted to output position coordinates of said at least one data point 220 relative to at least a portion of said target context (double headed arrow 250). Module 300 is described in greater detail hereinbelow with reference to FIG. 3.

In some exemplary embodiments of the invention, position coordinates of at least one data point 220 are defined relative to target marker 230. In some exemplary embodiments of system 200, tool 221 and marker 230 each independently report to or are measured by module 300. In other exemplary embodiments of system 200, tool 221 or marker 230 determines a relative position of these two items and reports to module 300.

In some exemplary embodiments of the invention, registration module 300 comprises analytic circuitry adapted to receive a first data input including a position of target marker 230 relative to external marker(s) 210, 212, 214 and 216 and a second data input comprising a relative position of data acquisition tool 221 with respect to target marker 230 and process the two data inputs to produce output 250. Optionally, module 300 receives individual absolute locations of markers 210, 212, 214 and 216 and 230 and/or tool 221 as data inputs and computes relative locations as needed.

In some exemplary embodiments of the invention, registration module 300 is provided as software configured for installation on a computer and/or personal digital assistant and/or remote server.

The phrase "at least a portion of said target context" as used in this specification and the accompanying claims refers to a location of at least one of the external markers. In some exemplary embodiments of the invention, two or three or more external markers are employed. In other exemplary embodiments of the invention, a single external marker is employed. In the depicted embodiment, four external markers are present (210, 212, 214 and 216).

The term "surface" as used in this specification and the accompanying claims refers to a theoretical surface of an object. In actual practice, measurements of a surface may be conducted at a depth below the surface and be considered indicative of the surface, For example, margin status in a breast biopsy is typically evaluated based upon measurements taken at a depth of 1 mm with respect to a surface of a removed lump.

In some exemplary embodiments of the invention, 220 is on the surface of target

520. In other exemplary embodiments of the invention, 220 is at a depth below surface 521 of target 520. In either case, 220 can be "transformed" to corresponding point 222. on an inner surface 522 of a cavity formed by excision of target 520 and/or within the cavity.

Optionally, system 200 comprises a reporting module 270. In some exemplary embodiments of the invention, reporting module 270 presents the output (e.g. 160) visually, for example on a display screen 290. In some exemplary embodiments of the invention, reporting module 270 presents the output audibly, for example by speaker 295. In some exemplary embodiments of the invention, reporting module 270 presents the output numerically, optionally also in machine readable form (e.g. as digital data stored in a memory, as digital data transmitted by wire or wireless media). Alternatively or additionally, system 200 comprises a guidance module 280 adapted to receive the output of registration module 300 and position coordinates of an operative device (not pictured) and issue guidance instructions to guide said operative device to a location 222 in target context 522 corresponding to data point 220 on surface 521 of target 520. Optionally, the operative device can include one or more of a cutting tool, a cauterization tool, an ablation tool (e.g. a cryo-ablation tool, an RF ablation tool), an ultrasound cavitation device, a dispensing tool, a radiation administration tool, a laser beam, a brachytherapy delivery device or an external beam radiation source. In some exemplary embodiments of the invention, a dispensing device delivers one or more of a liquid, a gel, a suspension, a solid, a powder and a particle to location 222.

In some exemplary embodiments of the invention, guidance module 280 presents guidance instructions visually, for example on a display screen 290. In some exemplary embodiments of the invention, guidance module 280 presents guidance instructions audibly, for example by speaker 295.

In some exemplary embodiments of the invention, guiding module 280 controls a robotic or other mechanical or electromechanical device to guide the tool to location 222.

Exemplary Mapping Registration Apparatus

FIG. 3 is a schematic representation of a mapping registration apparatus 300. Optionally, apparatus 300 serves as a registration module in system 200. Depicted exemplary apparatus 300 includes a context determination module 310 configured to determine a location of target marker 230 in target 520 relative to at least one contextual marker 210 and/or 212 and/or 214 and/or 216 outside target 230.

According to various exemplary embodiments of the invention, module 310 receives location of target marker 230 in target 520 relative to at least one contextual marker 210 and/or 212 and/or 214 and/or 216 outside target 230 as processed data (e.g. from an ultrasound transducer or computerized tomography unit) and/or calculates relative location of target marker 230 in target 520 relative to one or more of contextual markers 210, 212, 214 and 216 from absolute position coordinates. According to various exemplary embodiments of the invention, module 310 determines location of passive markers and/or receives input from active markers and/or receives feedback from passive markers (e.g. ultrasound reflection).

Optionally, context determination module 310 outputs a series of relative locations to a memory 330. Depicted exemplary apparatus 300 includes a data receiver 320 configured to receive absolute position coordinates for at least one data point 220 on a surface of target 520 and/or relative position coordinates of point 220 defined with reference to target marker 230. Relative position coordinates of point 220 with reference to target marker 230 are relayed by data receiver 320 to memory 330. Depicted exemplary analytic circuitry 340 is adapted to receive data stored in memory 330 and transform said relative position coordinates of data point 220 to translated coordinates 340' defined relative to at least one of the contextual markers (e.g. 210, 212, 214 and 216 in FIG. 2). In some exemplary embodiments of the invention, the translated coordinates are provided as an output signal, for example via reporting module 270 (FIG. 2).

Exemplary Calculation Mode

FIG. 4 is a schematic representation 400 of addition of vectors with two different origins which illustrates the operative principle of exemplary embodiments of the invention described above. In FIG. 4, A corresponds to an external marker or contextual marker (e.g. 216) located outside target 520 and B corresponds to a target marker located within target 520 (e.g. 230). C corresponds to data point 220 on surface 521 of target 520 and its corresponding point 222 on inner surface 522 in the cavity created by removal of target 520. While target 520 is still located in situ, vector V1 (A-B) with origin A and coordinate system Xi, Yi1 Zi is determined and defined as a distance (D1), an angle of elevation (θi) and an angle of rotation (Φi) around the Yi axis.

At this stage, a spatial relationship between target 520 and part, optionally all, of its surrounding context can be altered. Following this change on spatial relationship, vector V2 (B-C) with origin B and coordinate system X2, Y2; Z2 is determined and defined as a distance (D2), an angle of elevation (θ2) and an angle of rotation (Φ2) around the Y2 axis. V2 defines the location of data point 220 relative to target marker 230.

Using vectorial addition, it is possible to calculate V3 which defines a location 222 on an inner surface 522 of a cavity 514 and/or a location 222 relative to "body" created by repositioning of target 520 relative to contextual marker 216 located at A using EQUATION 1.

$$V3 = V1 + V2 \quad \text{EQUATION 1}$$

The resultant V3 is more simply described by EQUATION 2:

$$V3 = V3(D3, \theta3, \Phi3) \quad \text{EQUATION 2}$$

Where V3 (A-C) is measured relative to A and coordinate system X1, Y1, Z1, and is presented as a distance (D1), an angle of elevation (G1) and an angle of rotation (O1) around the Y1 axis.

Similar calculations can be done in Cartesian or other coordinate systems. Optionally and additionally, the orientation of contextual (e.g. 216) and internal (e.g. 23) markers is "registered" (that is 5-D position and orientation of marker). To provide for the correct determination of V2 with regards to V1, and to provide for the correct determination of V3 with regards to V1.

Using this type of calculation, system 200 can operate using first and second data inputs including vectorial position information where each vector is expressed as a distance, an angle of elevation and an angle of rotation.

Alternatively or additionally, using this type of calculation, method 100 can be performed with a location of a target marker relative to one or more contextual markers expressed as a distance, an angle of elevation and an angle of rotation. In some exemplary embodiments of the invention, an apparatus 300 as described above is adapted to define relative locations in terms of distance, angle of elevation and angle of rotation and/or position coordinates relative to a target marker (e.g. 230) for at least one data point (e.g. 220) on a surface (e.g. 521) of a target (e.g. 520) are defined in terms of distance, angle of elevation and angle of rotation is provided as part of system 200 and/or is used to implement method 100.

Exemplary clinical use scenario FIGS. 5A and 5B are schematic representations illustrating exemplary spatial relationships 500 and 501 respectively of position indicators before and after excision of a tissue sample. For purposes of illustration contextual tissue 510 will be described as a breast containing a target 520 including tumor tissue to be excised. It is stressed that contextual tissue 510 could also be a liver, kidney, lung, brain, prostate or other tissue. FIG. 5A shows an arrow from target marker 230 to contextual marker 216 corresponding to V1 of FIG. 4. Determination of V1 can be accomplished using any means known in the art. Although a single V1 is depicted for clarity, a series Of V1 Vn are determined where n is the number of contextual markers employed. In the depicted example four Vi are determined between target marker 230 and each of external contextual markers 210, 212, 214 and 216.

At this stage, target 520 is at least partially exposed, optionally excised, and positions of one or more data points 220 (corresponding to point C in FIG. 4) on surface 521 of target 520 are determined relative to target marker 230 as described hereinabove with regard to FIG. 2. In some exemplary embodiments of the invention, positions of data points 220 are defined as vectors V2.

A single V2 is depicted in FIG. 5a between target marker 230 and an exemplary data point 220 for clarity. Typically a series of V2 Vm are determined where m is the number of data points 220. In addition to locational information regarding data points 220, clinical information is also collected. Clinical information can include one or more of pathology data (e.g. cytologic evaluation, morphological evaluation), analysis of magnetic and/or electromagnetic properties and chemical or biochemical analysis (e.g. presence and/or level of a tumor marker).

Optionally, position and/or clinical information of data points 220 can be determined at the operating room and/or at a pathology lab. In some exemplary embodiments of the invention, position and clinical information of data points 220 is determined during surgery (e.g. using a probe manufactured by Dune Medical; Israel) Alternatively or additionally, clinical information is linked to position information of data points 220 during pathological evaluation or other post-surgery diagnostic procedures (e.g. imaging and/or genetic analysis and/or molecular biology analysis of removed target).

In some exemplary embodiments of the invention, the clinical information is available substantially immediately and is relayed directly from tool 221 (FIG. 2) to registration module 300 together with positional information. Optionally, additional procedures can be performed by employment of the additional operative device, substantially immediately at location(s) 222.

In other exemplary embodiments of the invention, marking/labeling of a pathological section for position occurs when it is cut from the target, and clinical pathology data is linked to it when it becomes available, generating a data point 220 with clinical data. According to these embodiments of the invention, position and clinical information are not obtained at the same time and place. Optionally, these embodiments are useful when a pathological evaluation procedure is destructive with regards to keeping positional registration of what was sampled for pathology relative to the originally excised target.

In some exemplary embodiments of the invention, only position data of 520 relative to 230 is obtained. Optionally, target marker 230 is inserted at the pathology lab. In this case, there is no dual registration, just positional registration of surface 520 data relative to target marker 230. Typically, a large number of data points 220 are analyzed with respect to one or more clinical parameters and their locations relative to target marker 230 are recorded as vectors V2. In those cases where one or more data points 220 indicate that a point, optionally, a region, on surface 521 of target 520 requires additional clinical and/or diagnostic action (e.g. analysis, removal, ablation, radiation, medication), calculation of one or more vectors V3 as described hereinabove is undertaken to a identify one or more points 222 on inner surface 522 of the cavity created by removal of target 520. Optionally, a group of points 222 defines a region on inner surface 522 which should be further investigated and/or removed.

Data from 220 and/or 222 can be used for planning further treatment. For example, based on 220/222 data radiation dose administration and/or spatial variation is determined, ablation profile (depth, and power) and/or spatial variation is determined, local medication dose distribution and/or spatial variation is determined.

Sensors 210 and/or 212 and/or 214 and/or 216 can be used to guide the implementation of a further treatment plan, by identifying V3 and 222, and providing spatial registration/localization information to a guide an additional treatment and/or diagnostic tool so that a treatment plan is performed as desired. Sensors 210 and/or 212 and/or 214 and/or 216 can be used to guide the implementation of a further treatment plan, by identifying the "location" of 230, that is the location where 230 was before it was removed, and providing spatial registration/localization information to an additional treatment tool so that a treatment plan is performed as desired.

Sensors 210 and/or 212 and/or 214 and/or 216 can be used to guide the implementation of a further treatment plan, by identifying changes in the volumetric state of the treated body tissue portion relative to when diagnostic and/or surgical related data was obtained, and providing spatial registration/localization information to an additional treatment tool so that a treatment plan is performed as desired. This can also be performed by comparing the relative positions of sensors 210 and/or 212 and/or 214 and/or 216 in various stages of the diagnostic/surgical/treatment procedures.

FIG. 7 depicts an exemplary embodiments of the invention, in which an additional treatment tool includes a "further treatment machine" (FTM) generally indicated as 700. In some exemplary embodiments of the invention, FTM 700 is provided as balloon or malleable sac adapted to fill cavity 514. Optionally, FTM 700 includes position registration capabilities. In some exemplary embodiments of the invention, the position registration capability enables, by obtaining the location of 700 relative to sensors 210 and/or 212 and/or 214 and/or 216, identification of the relative position of FTM 700 relative to where target marker 230 was when target 540 occupied cavity 514. In FIG. 7, FTM 700 is depicted superimposed on target 540 containing target marker 230. Center 730, optionally including an internal FTM marker, is offset from 230 by a vectorial displacement indicated as V4.

Optionally, FTM 700 includes a local radiation administration device (e.g. balloon and/or cone) which has a rounded geometry, usually roughly spherical. Optionally, the geometry of surface 724 of FTM 700 conforms to cavity 514, for example by inflation. Optionally, FTM 700 includes an ablation device and/or a resection tool (e.g. knife, electro-surgical cutter).

Since treatment by FTM 700 may be relative to its own coordinates, an additional registration based upon V4 can be implemented to differentially direct treatment based on the relative distance and/or angle between the location where 230 was and different locations of 522. In this case, identification of 222 (and thus 220) is not required. Optionally, and additionally, the additional registration based upon V4 can also be implemented to direct treatment to one or more desired locations 222 on an inner surface 522 of a cavity 514 (see FIG. 5).

Balloons for application of localized radiation are available commercially and will be easily incorporated into exemplary embodiments of the present invention by one of ordinary skill in the art. Commercially available products of this type include, but are not limited to, Contura multi lumen balloon (SenoRx, Inc., Aliso Viejo, Calif., USA); MammoSite Balloon Catheter (CYTYC; Hologic, Bedford Mass., USA) and SAVI applicator (Cianna Medical, Aliso Viejo, Calif., USA). These commercially available balloons can serve as FTM 700 in some exemplary embodiments of the invention. FIG. 5B shows contextual breast tissue 510 after removal of a target lump 520 suspected as being malignant. Incision 512 has caused a portion 511 of the contextual tissue to be shifted and removal of target lump 620 has created a cavity 514. Original surface 521 contours of target 520 do not completely conform to inner surface 522 of cavity 514. According to exemplary embodiments of the invention, registration module 300 selects one or more contextual markers which comprise at least a portion of said target context for calculation of one or more V3 vectors to locate one or more corresponding points 222 on inner surface 522 of cavity 514. Optionally, registration module 300 selects contextual marker(s) for calculation of V3 vectors based upon analysis of the value of the D component (or magnitude) of the vectors. In some exemplary embodiments of the invention, V3 with smaller D3 values are included and/or V3 with larger D3 values are excluded by module 300. Optionally, registration module 300 selects contextual marker(s) for calculation of V3 vectors based upon analysis of the change in the position of contextual marker, relative to a fixed body coordinate/location marker, as compared to the positions during the removal of 520. In some exemplary embodiments of the invention, V3 for which the change in position was the smallest are selected. In some exemplary embodiments of the invention, V3 is calculated relative to contextual marker(s) located on a fixed body coordinate/location.

Exemplary Contextual Position Indicator

FIG. 6 is a schematic representation of an exemplary contextual position indicator 600 according to some embodiments of the invention. Depicted exemplary indicator 600 includes a position indication module 610 adapted to provide a position output signal 652. Although the depicted module 610 actively provides signal 652, modules which passively receive an external signal and translate it into positional information may also be employed in some exemplary embodiments of the invention.

According to various embodiments of the invention, module 610 can employ any active or passive marker technology known in the art. Optionally, contextual position indicator 600 and/or 230 are coded and/or labeled to enable selective actuation and/or query and/or identification from specific indicators.

Depicted exemplary indicator 600 includes a signal port 620 adapted to relay signal 652 to an external device, such as registration module 300 of system 200 as described hereinabove and an adhesive surface 630 adapted to adhere to a subject.

Optionally, adhesive surface 630 is provided as a crack and peel surface with a removable cover 632.

Optionally, indicator 600 is adapted for fixed, accurate, placement. In some exemplary embodiments of the invention, indicator 600 remains in a fixed position for 14-21 days or intermediate or larger numbers of days. This ability to remain in a same position allows acquisition of additional clinical data, for example biopsy results. These additional results can be useful in re-operation and/or radiation treatment.

Alternatively or additionally, the ability to remain in a same position allows for monitoring of volumetric changes during various stages of diagnostic and/or treatment. Optionally, these volumetric changes are identified and obtained by comparing the relative positions of contextual sensors to each other, between various stages of diagnostic and/or treatment. Information on the volumetric changes can be used to correct for spatial variations in tissue position, between various stages of diagnostic and/or treatment. Volumetric information is important for correlating spatially tagged data, and/or imaging data between various stages of diagnostic and/or treatment. This ability of indicators 600 to remain in a same position allows for use of positional and clinical data obtained on 520 to guide additional treatment and/or procedures (e.g. reoperation, radiation) on 522, by transforming the locations 220 to locations 222, relative to sensors 600.

In some exemplary embodiments of the invention, position output signal 652 defines a relative position of at least one other position indicator relative to the contextual position indicator. For example, if indicator 600 represents indicator 216 in FIG. 2, signal 652 includes relative positional information pertaining to one or more of indicators 214, 212 and 210 relative to the contextual position indicator 216 providing signal 652.

In some exemplary embodiments of the invention, signal 652 is relayed via a physical connection 640 fitted with suitable connectors 642 and 644. Connection 640 is optionally provided as a wire, a fiber optic connection or any other means known in the art. In those embodiments of the invention which employ physical connection 640, connector 644 is adapted to match port 620 and connector 642 is adapted to match an additional port 643 provided on external device 300. Optionally, port 640 is reversible attachable/detachable.

In other exemplary embodiments of the invention, signal port 620 relays output signal 652 to external device 300 via a wireless connection. Wireless connections include, but are not limited to, WIFI, Bluetooth, infrared, microwave and RF (radio frequency) connections. Optionally, external device 300 is equipped with an antenna 650 which receives signal 652.

Exemplary Position Indicator Types

US 2004/0243148 by Wasielewski (paragraphs 0087-0103) serves as a review of source and sourceless sensors including examples of commercially available products based on Wasielewski. These portions of Wiselewski are summarized here to generally indicate technologies which one of ordinary skill in the art would be expected to incorporate into the context of various exemplary embodiments of the invention using this specification.

Current technology in reference sensors such as that disclosed in U.S. patent application Publication Nos. 2002/0180306 and 2002/0104376, the disclosures of which are hereby incorporated by reference, evidences substantial development in reducing the size of such sensors utilizing nanotechnology.

The exemplary sensors discussed herein and adapted for use in the context of exemplary embodiments of the invention may fall within generally two classes: source and source-less. Source sensors rely on artificial stimuli such as generated magnetic fields or outputs from other artificial devices for one or more points of reference. In exemplary form, a pair of source sensors may rely on each other for relative points of reference. In a further exemplary form, a first sensor may be mounted to a first object and a reference sensor may be mounted to a second object, where the first sensor utilizes a magnetic field or other output generated by the reference sensor to provide a reference point as to the movement of the second sensor with respect to the first sensor. Likewise, the reference sensor may utilize a magnetic field or other output from the first sensor as a reference point as to the movement of the reference sensor with respect to the first sensor. In this manner, a surgeon is able to manipulate a first object having the first sensor mounted thereto with respect to the second object with the second sensor mounted thereto without necessitating a direct line of sight to position the first object in relation to the second object.

A second class of sensors, source-less sensors, relies on natural or ever-present stimuli such as the earth's magnetic field or gravity. Exemplary source-less sensors may utilize the magnetic field and/or gravity of the earth to provide a fixed reference point for measurements such as tilt and level. Such sensors may be self-contained and, unlike some source sensors, do not require a transducer to create an artificial stimulus or field.

One exemplary sensor technology available for use in the context of exemplary embodiments of the invention is the Flock of Birds, and more specifically, the microBIRD technology commercially available from Ascension Technology Corporation (see http://wwwDOTascension-techDOTcom/products/microbird.php), and patented in U.S. Pat. Nos. 4,849,692 and 4,945,305, the disclosures of which are incorporated herein by reference. Flock of Birds is a magnetic-transducing technique that measures the position and orientation of one or more receiving antenna sensors located on the surgical device, tool, prosthetic component, or implant with respect to a transmitter located on a reference object. The transmitter includes three individual antennae arranged concentrically to generate a multiplicity of DC magnetic fields that are picked up by the sensor. The sensor measures the position and orientation of the object which carries it. The sensor consists of three axes of antenna that are sensitive to DC magnetic fields. The transmitter includes a driver that provides a controlled amount of DC current to each axis of the transmitter.

The signal output from the sensor is transmitted back to the conditioning hardware and software of the display system which conditions and processes the signal to compute position and orientation of the sensor with respect to the transmitter using the Flock of Birds available algorithms. Such position and orientation data can then be used to generate a visual signal to be displayed.

A second exemplary sensor technology suitable for use in exemplary embodiments of the invention includes micro-gyroscopes to measure angular rate; i.e., how quickly an object turns. The rotation is typically measured with reference to one of three axes: X, Y, and Z or yaw, pitch, and roll. A micro-gyroscope with one axis of sensitivity can also be used to measure other axes by mounting the micro-gyroscope differently, as shown. For example, a yaw-axis micro-gyroscope is mounted on its side so that the yaw axis becomes the roll axis. Depending on how a micro-gyroscope is mounted, its primary axis of sensitivity can be one of the three axes of motion: yaw, pitch, or roll. Exemplary micro-gyroscopes for use in the context of embodiments of the invention include ADXRS 150 available from Analog Devices (http://wwwDOTanalogDOTcom).

Such exemplary micro-gyroscopes are rotational rate measurement systems on a single monolithic integrated circuit. The exemplary micro-gyroscopes measure angular rate by means of Coriolis acceleration. Each of three micro-gyroscopes may be oriented with respect to the surgical device, tool, prosthetic component, or implant so that each of the X, Y, and Z planes is accommodated.

One practical application is to measure how quickly a surgical instrument is turned by mounting one or more micro-gyroscopes thereto. In addition, the angular rate can be integrated over time to determine angular position. For example, if a micro-gyroscope senses that the surgical instrument is out of position, an appropriate signal may indicate such to the surgeon and discontinue operation of the instrument until the instrument is oriented in a proper manner. An exemplary micro-gyroscope includes a frame containing a resonating mass tethered to a substrate by springs at 90° relative to the resonating motion to measure the Coriolis acceleration. A plurality of Coriolis sense fingers are used to capacitively sense displacement of the frame in response to the force exerted by the mass. If the springs have stiffness, K, then the displacement resulting from the reaction force will be $2\Omega vM/K$. As the rate of rotation with respect to the micro-gyroscope increases, so does the displacement of the mass and the signal derived from the corresponding capacitance change. It should be noted that the micro-gyroscope may be mounted anywhere on the surgical device, tool, prosthetic component, or implant and at any angle, so long as the sensing axis of the micro-gyroscope is parallel to the axis of rotation. The micro-gyroscopes measure the displacement of the resonating mass and its frame due to the Coriolis effect through capacitive sensing elements attached to a resonator. Displacement due to angular rate induces a differential capacitance in this system. If the total capacitance is C and the spacing of the sense fingers is "g", then the differential capacitance is $2\Omega vMC/gK$, and is directly proportional to the angular rate. The fidelity of this relationship is excellent in practice, with nonlinearity less than 0.1%.

The micro-gyroscopes can sense capacitance changes as small as $12\times10^{-}$<farads (12 zeptofarads) from deflections as small as 0.00016 Angstroms (16 femtometers). This can be utilized in the surgical device, tool, prosthetic component, or implant by situating the electronics, including amplifiers and filters, on the same die as the gyroscope. The differential signal alternates at the resonator frequency and can be extracted from the noise by correlation.

The exemplary ADXRS micro-gyroscopes employ two resonators that operate anti-phase to differentially sense signals and reject common-mode external accelerations that are unrelated to angular motion to angular rate-sensing that makes it possible to reject shocks of up to 1,000 g. As a result, the micro-gyroscopes measure the same magnitude of rotation, but give outputs in opposite directions. Therefore, the difference between the two outputs is used to measure angular rate. This cancels non-rotational signals that affect both ends of the micro-gyroscope.

Accelerometers may also be utilized as sensors in some exemplary embodiments of the invention to measure tilt or inclination, inertial forces, and shock or vibration. An intended application for accelerometers with respect to some exemplary embodiments of the invention includes measurinGUilt in at least one axis and exemplary accelerometers are available as model ADXL203BE from Analog Devices (http://wwwDOTanalogDOTcom). Such exemplary accelerometers are acceleration measurement systems on a single monolithic integrated circuit to implement an open loop acceleration measurement architecture. It is envisioned that the accelerometer be oriented with respect to the surgical device, tool, prosthetic component, or implant so the accelerometer's X and Y axis would most often approach a parallel orientation with respect to the earth's surface. In such an orientation, tilt may be measured in two axes for roll and pitch. In addition to measuring acceleration, the acceleration may be integrated over time to provide velocity data, which can likewise be integrated over time to provide position data. Those of ordinary skill are familiar with the noise considerations associated with power supplies for sensors, and in particular, accelerometers. Some exemplary embodiments of the invention, utilize a capacitor, generally around 1 µF, to decouple the accelerometer from the noise of the power supply. Other techniques may include adding a resistor in series with the power supply or adding a bulk capacitor (in the 1 µF to 4 µF range) in parallel with the first capacitor (1 µF).

Other exemplary accelerometers include model KXG20-L20 available from Kionix, Inc. (http://wwwDOTkionixDOTcom), model SCA610 Series available from VTI Technologies Oy (http://wwwDOTvtiDOTfi), model SQ-XL-DAQ from (http://signalquest.com). The SQ-XL-DAQ functions as a self contained data acquisition system for 2 axis or 3 axis acceleration, tilt, and vibration measurement when used with a serial interface cable.

Accelerometers can optionally be used in combination with gyroscopes, where gyroscopes detect rotation and where the accelerometers detect acceleration, for sensing inertial movement within a three-dimensional space.

In some exemplary embodiments of the invention sensors include inclinometers to measure roll angle and pitch angle in one or more of the exemplary embodiments discussed above. An exemplary inclinometer for use in the context of exemplary embodiments of the invention is model SQ-S12X-360DA from Signal Quest, Inc. (http://wwwDOTSignalquestDOTcom). Such an exemplary inclinometer provides both an analog voltage output and a digital serial output corresponding directly to a full-scale range of 360° of pitch angle and 180° of roll angle. Another exemplary inclinometer for use in the context of exemplary embodiments of the invention is model SCA61T Series available from VTI Technologies Oy (http://wwwDOTvtiDOTfi). The measuring direction for this exemplary inclinometer is parallel to the mounting plane.

In some exemplary embodiments of the invention, the sensors include magnetometers for detecting an artificial magnetic field and/or the earth's magnetic field and discerning positional data therefrom. An exemplary magnetometer for use in the context of exemplary embodiments of the invention is model CXM544 available from Crossbow Technology, Inc. (http://wwwDOTxbowDOTcom). The magnetometer is capable of detecting the earth's magnetic field in three axes and computes a continuous measure of orientation using a 3-axis accelerometer as a gravitational reference field. The magnetometer compensates for temperature drift, alignment, and other errors.

Another magnetometer suitable for use in exemplary embodiments of the invention is model HMC 1053 available from Honeywell, Inc. (http://wwwDOTmagneticsensorsDOTcom). This type of magnetometer includes a wheatstone bridge to measure magnetic fields. With power supply applied to a bridge, the sensor converts any incident magnetic field in the sensitive axis direction to a differential voltage output, hi addition to the bridge circuit, the sensor has two on-chip magnetically coupled straps; the offset strap and the set/reset strap. These straps are for incident field adjustment and magnetic domain alignment, and eliminate the need for external coils positioned around the sensors. The magnetoresistive sensors are made of a nickel-iron (Permalloy) thin-film deposited on a silicon wafer and patterned as a resistive strip element. In the presence of a magnetic field, a change in the bridge resistive elements causes a corresponding change in voltage across the bridge outputs. These resistive elements are aligned together to have a common sensitive axis (indicated by arrows) that will provide positive voltage change with magnetic fields increasing in the sensitive direction. Because the output only is in proportion to the one-dimensional axis (the principle of anisotropy) and its magnitude, additional sensor bridges placed at orthogonal directions permit accurate measurement of arbitrary field direction. The combination of sensor bridges in two and three orthogonal axes permits applications such as compassing and magnetometry.

In other exemplary embodiments of the invention, a three-axis magnetic field detector includes a two-axis detector combined with a single axis detector. Alternatively a single three axes detector may be used in place of the above combination.

Exemplary System Configurations

Referring again to FIG. 2, different exemplary configurations of system 200 are described in general terms using expressions and terms consistent with those hereinabove.

In some exemplary embodiments of the invention, active external contextual markers are employed. Active markers suitable for use in this context include, but are not limited to ultrasound transmitters and/or transducers, RF signal sources, magnetic field sources, and microwave signal sources. In other exemplary embodiments of the invention, passive external contextual markers are employed. Passive markers suitable for use in this context include, but are not limited to ultrasound reflectors and/or receivers, RF receivers and microwave receivers.

In still other exemplary embodiments of the invention, passive external contextual markers are employed. Passive markers suitable for use in this context include, but are not limited to objects which are opaque with regard a relevant sensing technology. When passive contextual markers are employed, context determination module 310 and/or target marker 230 are adapted to actively determine absolute and/or relative locations of the external contextual markers. Alternatively or additionally:

In some exemplary embodiments of the invention, target marker 230 actively produces a signal indicative of its location. Active markers suitable for use in this context include, but are not limited to, ultrasound transmitters, RF signal sources, magnetic field sources, and microwave signal sources. In other exemplary embodiments of the invention, target marker 230 passively indicates its position. Passive indication in this context includes, but is not limited to, ultrasound reflections and/or reception, RF reception and microwave reception.

In still other exemplary embodiments of the invention, target marker 230 is provided as a passive marker which is located relative the external contextual markers and/or point 220 by context determination module 310 and/or is located relative to point 220 by tool 221. Passive markers suitable for use in this context include, but are not limited to objects which are opaque with regard a relevant sensing technology. When a passive target marker 230 is employed, context determination module 310 and/or tool 221 are adapted to actively determine absolute and/or relative locations of the target marker 230.

In some exemplary embodiments of the invention, contextual (external) markers are of a type which does not require a line-of-sight between transmitter and/or receiver and markers (e.g. example, magnetic sensors, accelerometers).

In some exemplary embodiments of the invention, external and/or target markers which can provide absolute position and or angular orientation instead of or in addition to changes in position and or orientation are employed (e.g., optical position sensors, magnetic position sensors).

Exemplary Guidance Systems

Robotic guidance systems are commercially available from, for example, BrainLAB, Inc. (Westchester, Ill., USA). BrainLAB offers iPlan® Flow which enables physicians to pre-operatively plan spatial distribution of locally infused fluids in the brain using stereotactic planning and exact placement of fluid delivery catheters. iPlan Flow is an integral element the BrainLAB Intelligent Treatment Framework which makes calculation results across different applications—from surgical navigation using VectorVision® to radiation oncology using iPlan Radiotherapy.

Brainlab also offers optical tracking systems adapted to monitor exact location of surgical instruments relative to patients' boney anatomy. The operator can then navigate instruments to planned resection levels. This application is useful, for example, in knee and shoulder surgeries.

Additional robotic navigation solutions are provided by Accuray (Sunnyvale, Calif., USA) as part of CyberKnife® Robotic Radiosurgery System which employs image guidance technology and computer controlled robotics to continuously track a tumor, detect its location and correct for tumor and patient movement in real-time throughout treatment.

Academic research in surgical navigation guidance is exemplified by the

Computer Vision Group of the MIT (Massachusetts Institute of Technology, USA) Artificial Intelligence Lab's collaboration with the Surgical Planning Laboratory of Brigham and Women's Hospital (Boston, Mass., USA). The collaboration is developing tools to support image guided surgery which enable surgeons to visualize internal structures through an automated overlay of 3D reconstructions of internal anatomy on top of live video views of a patient. Sample applications are in preoperative surgical planning, intraoperative surgical guidance, navigation, and instrument tracking.

One of ordinary skill in the art will be able to incorporate existing robotic guidance solutions into the context of exemplary embodiments of the invention.

Exemplary Biopsy Devices

In some exemplary embodiments of the invention, target 520 is removed as part of a biopsy procedure. Commercially available biopsy tools suitable for use in these exemplary embodiments include, but are not limited to, Intact™ Breast Lesion Excision System (BLES) (Intact Medical Corporation, Natick, Mass., USA) Halo Breast Biopsy Device (Rubicor Medical, Inc., Redwood City, Calif., USA). One of ordinary skill in the art will be able to adapt these, or other, available biopsy tools for use in exemplary embodiments of the invention without undue experimentation.

Exemplary Use Scenarios

Referring again to FIG. 2, in some exemplary embodiments of the invention, data characterizing from one or more data points 220, target 520 is presented graphically, in a 2D or 3D presentation. This data may be, for example, target 520 margin status characterization data. Alternatively or additionally, corresponding cavity/intact tissue characterization data (e.g. from one or more corresponding points 222) is presented graphically, in a 2D or 3D presentation. This characterization data may be, for example, margin status characterization data. This is performed by use of relative positions to external markers 210 and/or 212 and/or 214 and/or 216. Optionally, graphic presentation occurs on display 290. 2D and or 3D data characterizing target 520 may be overlaid on a 2D and or 3D presentation of target 520 and or tissue portion 522. The presentation may be obtained from an imaging device. Alternatively, target 520 can be scanned with a data acquisition tool 221, to obtain the volumetric characterization (a 2D and or 3D presentation) of the surface of target 520. In some exemplary embodiments of the invention, data acquisition tool 221 is used to provide position coordinates of additional points on an external body surface (e.g. a breast) relative to one or more of the external and/or target markers described hereinabove. Optionally, this type of data contributes to subsequent tissue reconstruction, for example following removal of target 520.

Exemplary Positioning Strategy

In some exemplary embodiments of the invention, one or more external markers (e.g. 210; 212; 214 and 216) are spatially distributed with regard to target 520 so as to increase a probability that at least one external marker will be proximal to target 520 for any point 220 on the target surface. For example, the external markers can be distributed to at least partially surround target 520 in one or more planes.

In some exemplary embodiments of the invention, after target marker 230 is positioned, body contour 202 is scanned with data acquisition tool 221 to ascertain one or more desirable locations for contextual markers (e.g. 210; 212; 214 and 216). Optionally, audio and/or visual indications for placing the contextual markers are provided. Desirable locations for contextual markers (e.g. 210; 212; 214 and 216) may be selected for providing maximal solid angle coverage of contextual markers relative to target marker (s) 230, with minimal over-lap between the solid angle of each of the contextual markers. Optionally, this distribution contributes to improvement of solid angle coverage of contextual markers relative to target marker(s), using any given number of contextual markers. Optionally, guidance for positioning contextual markers at desirable locations may be by Audio and/or visual indications. According to various exemplary embodiments of the invention, target marker (s) 230 can be positioned before and/or during and/or after contextual markers (e.g. 210; 212; 214 and 216).

In some exemplary embodiments of the invention, after target marker 230 is positioned, target surface 521 is scanned with data acquisition tool 221 to ascertain the volumetric relation between body contour surface 202 and marker 230. This volumetric relation may be used for planning an incision path for removing target 520. In this case contextual markers are not needed.

In some exemplary embodiments of the invention at least one of the contextual markers is positioned on a fixed anatomic feature (e.g. a skeletal attachment point) position on/in the body. Optionally, positioning on a fixed anatomic feature contributes to an ability to evaluate volumetric changes in positions of other contextual markers.

In some exemplary embodiments of the invention, markers 230 and/or 210 and/or 212 and/or 214 and/or 216 are provided as biodegradable and/or resorbable markers. In some exemplary embodiments of the invention, calibration and/or registration of absolute position (relative to a subject's body) of marker 230 inserted into the body (i.e. biopsy marker) is performed using contextual markers 210 and/or 212 and/or 214 and/or 216 on the subject's body (e.g. breast). Optionally, this calibration can be used to monitor drift of marker 230 over time.

Alternatively or additionally, a location of target 520, based on diagnostic data is performed so that a wire guided placement of marker 230 can be accurately performed. Optionally, data from a previously placed target marker 230 and or contextual markers (e.g. 210; 212; 214 and 216) is useful in planning an insertion path for the wire guide. In some exemplary embodiments of the invention, this is useful in cosmesis. Optionally, wire guiding of an additional marker 230 is not performed and a surgical tool is guided based upon data provided by the biopsy marker 230.

Additional Exemplary Embodiments

FIG. 8A depicts a transverse cross section of a target 520 and a single contextual marker 210.

FIG. 8B illustrates an exemplary procedure in which contextual markers e.g. 210 and/or 214) are positioned around target 520. In the depicted embodiment a "shape and orientation preserving" biopsy tool 810 including a target marker 230 is inserted and biopsy target 520 is excised. In this embodiment, target marker 230 is not on target 520 per se, but is held in a fixed relationship to target 520 by biopsy tool 810. Biopsy catheter 820 is optionally left in place and can provide an additional contextual marker 214.

According to the depicted embodiment, a position of biopsy tool 810 can be registered to points in cavity 514 since the shape and orientation of target 520 with respect to tool 810 are known. This makes it possible to calculate the position of target 520 as indicated by marker 230 on tool 810 relative to contextual marker 210 and/or 214 and/or any point 220 on target 520 using calculations described hereinabove. Optionally, after removal of target 520, clinical data for one or more points 220 is provided in conjunction with position coordinates as described hereinabove.

Using dual registration as described above, any problematic point 220 can be translated into a corresponding position 222 (FIG. 8C) on an inner wall of cavity 514. Optionally further treatment machine 700 is used to address identified point 222 on the inner wall of cavity 514. According to various embodiments of the invention, FTM 700 can excise tissue and/or ablate tissue and/or irradiate tissue and/or deliver medication to tissue.

Optionally FTM 700 is used to remove additional tissue, at one or more desired locations 222 on an inner surface 522 of a cavity 514. That is, the location of 222 relative to the FTM is identified by use of V4, V1, and V2 as described above.

In additional exemplary embodiments of the invention an angle resolved catheter 820 (FIG. 8B) is inserted to a biopsy site and biopsy tool 810 including on marker 730 is inserted via the catheter. In this exemplary embodiment, the catheter 820 provides a contextual marker 214 and relative position of biopsy tool 810 and FTM 700 is obtained directly relative to catheter 820 which serves as the (0,0,0) of the coordinate system. Optionally, only a single contextual marker (e.g. 210 or 214) is employed.

Optionally, following removal of target 520, shape of cavity 514 is "preserved", by, for example, filling with liquid and/or pressurized inert gas and/or inserting a supportive structure (e.g. cage and/or stent).

It is expected that during the life of this patent many types of position indicators will be developed and the scope of the invention is intended to include all such new technologies a priori.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

Specifically, a variety of numerical indicators have been utilized. It should be understood that these numerical indicators could vary even further based upon a variety of engineering principles, materials, intended use and designs incorporated into the invention. Additionally, components and/or actions ascribed to exemplary embodiments of the invention and depicted as a single unit may be divided into subunits. Conversely, components and/or actions ascribed to exemplary embodiments of the invention and depicted as subunits/individual actions may be combined into a single unit/action with the described/depicted function. Alternatively, or additionally, features used to describe a method can be used to characterize an apparatus or system and features used to describe an apparatus or system can be used to characterize a method.

It should be further understood that the individual features described hereinabove can be combined in all possible combinations and sub-combinations to produce additional embodiments of the invention. The examples given above are purely illustrative in nature and are not intended to limit the scope of the invention which is defined solely by the following claims. Specifically, the invention has been described in a medical context but might also be used in mining.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

The terms "include", and "have" and their conjugates as used herein mean "including but not necessarily limited to".

While this invention has been particularly shown and described with references to preferred embodiments thereof, it will be understood by those skilled in the art that various changes in form and details may be made therein without departing from the scope of the invention encompassed by the appended claims.

What is claimed is:

1. A mapping system for mapping a target, the system comprising:
   (a) at least two markers adapted to be differently positioned with respect to a target mass being mapped, said at least two markers comprising:
      (i) at least one external marker adapted for positioning outside the target mass and defining a target context that indicates a target position and orientation with respect to a surrounding area around said target mass, and
      (ii) at least one target marker adapted for fixed positioning on the target mass, within the target mass, or at a fixed spatial relationship with respect to the target mass;
   (b) a data acquisition module configured to provide data indicative of measured position coordinates for at least one data point at said target mass; and
   (c) a registration module connected to the data acquisition module and adapted to (i) receive said data indicative of the position coordinates for the at least one data point; (ii) determine, by utilizing position data of the at least one target marker relative to the at least one external marker, position coordinates of said at least one data point relative to at least a portion of said target context; and (iii) generate output data indicative of a location relative to said surrounding area, said location matching said data point at said target mass and being different therefrom.

2. A system according to claim 1, wherein said at least one data point at said target mass corresponds to at least one point on an exposed surface of said target mass.

3. A system according to claim 1, wherein said position coordinates of said at least one data point provided by said data acquisition module are defined relative to said at least one target marker.

4. A system according to claim 1, wherein said at least one external marker comprises at least three external markers.

5. A system according to claim 1, wherein said registration module comprises:
   a context determination module configured to (1) determine position coordinates of said at least one target marker relative to said at least one external marker, and (2) generate first output data indicative of said position coordinates;
   a data receiver module configured to (1) receive, from said data acquisition module, second data of position coordinates for the at least one data point relative to said at least one target marker, and (2) generate corresponding second output data; and
   an analytic circuitry comprising a data processor module configured to receive and process said first and second output data and determine coordinates of said at least one data point relative to the at least one portion of said target context.

6. A system according to claim 1, wherein said data acquisition module is configured to provide the position coordinates indicative of vectorial position information comprising a distance, an angle of elevation and an angle of rotation for said at least one data point at said target mass.

7. A system according to claim 1, wherein said data acquisition module is configured to provide the position coordinates comprising Cartesian coordinates.

8. A system according to claim 1, wherein said at least a portion of said target context includes at least one of said at least one external marker.

9. A system according to claim 1, comprising a reporting module connected to the registration module and configured for formatting said output data for presenting it visually on a display or audibly through a speaker.

10. A system according to claim 1, comprising:
 a guidance module adapted to:
  receive said output of said registration module and position coordinates of an operative device; and
  issue guidance instructions to guide said operative device to said location relative to said surrounding area matching said data point at said target mass.

11. A system according to claim 10, wherein said guidance module is configured and operable for generating data indicative of the guidance instructions comprising at least one of an audio signal and a visual signal.

12. A system according to claim 10, wherein said guidance module is configured and operable for generating data indicative of the guidance instructions comprising operating instructions for a robotic device.

\* \* \* \* \*